United States Patent
Hlavinka et al.

(10) Patent No.: US 8,016,736 B2
(45) Date of Patent: Sep. 13, 2011

(54) METHODS FOR WASHING A RED BLOOD CELL COMPONENT AND FOR REMOVING PRIONS THEREFROM

(75) Inventors: Dennis J. Hlavinka, Arvada, CO (US); Raymond P. Goodrich, Lakewood, CO (US); Eric T. Hansen, Thronton, CO (US)

(73) Assignee: CaridianBCT Biotechnologies, LLC, Lakewood, CO (US)

( * ) Notice: Subject to any disclaimer, the term of this patent is extended or adjusted under 35 U.S.C. 154(b) by 965 days.

(21) Appl. No.: 11/875,334

(22) Filed: Oct. 19, 2007

(65) Prior Publication Data

US 2008/0096750 A1    Apr. 24, 2008

Related U.S. Application Data

(60) Provisional application No. 60/853,397, filed on Oct. 20, 2006.

(51) Int. Cl.
*B04B 5/02* (2006.01)
*B04B 9/14* (2006.01)

(52) U.S. Cl. ............. 494/37; 494/16; 494/30; 604/4.01; 604/6.01

(58) Field of Classification Search ............... 424/93.7; 435/173.1, 173.2, 372; 494/16–21, 27–30, 494/33, 37, 45, 84; 604/4.01, 6.01
See application file for complete search history.

(56) References Cited

U.S. PATENT DOCUMENTS

| | | |
|---|---|---|
| 3,211,368 A | 10/1965 | Sbanely |
| 3,452,924 A | 7/1969 | Schultz |
| 3,640,388 A | 2/1972 | Ferrari |
| 3,718,133 A | 2/1973 | Perry et al. |
| 3,747,843 A | 7/1973 | Joyce |
| 3,921,898 A | 11/1975 | Finkel |
| 3,954,414 A | 5/1976 | Samson, Jr. et al. |
| 4,091,989 A | 5/1978 | Schlutz |
| 4,098,456 A | 7/1978 | Bayham |
| 4,157,781 A | 6/1979 | Maruyama |
| 4,191,469 A | 3/1980 | Flossdorf et al. |
| 4,296,882 A | 10/1981 | Kobayashi |
| 4,303,193 A | 12/1981 | Latham, Jr. |
| 4,412,831 A | 11/1983 | Avery et al. |
| 4,557,717 A | 12/1985 | Friedman |
| 4,767,397 A | 8/1988 | Hohenberg et al. |

(Continued)

FOREIGN PATENT DOCUMENTS

DE    20015684    2/2001

(Continued)

OTHER PUBLICATIONS

International Search Report for PCT/US2007/0081955, Apr. 7, 2008.

*Primary Examiner* — David A Reifsnyder
(74) *Attorney, Agent, or Firm* — Edna M. O'Connor; Laura Butterfield Arciniegas; John R. Merkling

(57) ABSTRACT

A method for washing multiple units of blood product including providing a centrifuge having a wash cell for each unit of blood product, balancing the centrifuge to accommodate for differences in the wash cells, and transferring supernatant including any wash solution from each unit of blood product on the centrifuge.

20 Claims, 11 Drawing Sheets

U.S. PATENT DOCUMENTS

| | | |
|---|---|---|
| 4,781,687 A | 11/1988 | Wall |
| 4,842,576 A | 6/1989 | Lysaght et al. |
| 4,850,952 A | 7/1989 | Figdor et al. |
| 4,887,411 A | 12/1989 | Rondeau et al. |
| 4,911,703 A | 3/1990 | Lysaght et al. |
| 4,919,646 A | 4/1990 | Perdriat |
| 4,939,081 A | 7/1990 | Figdor et al. |
| 5,651,766 A | 7/1997 | Kingsley et al. |
| 5,715,731 A | 2/1998 | Koch et al. |
| 5,728,060 A | 3/1998 | Kingsley et al. |
| 5,733,253 A | 3/1998 | Headley et al. |
| 5,770,069 A | 6/1998 | Meryman |
| 5,779,660 A | 7/1998 | Kingsley et al. |
| 5,788,621 A | 8/1998 | Eady |
| 5,853,382 A | 12/1998 | Kingsley et al. |
| 5,885,239 A | 3/1999 | Headley et al. |
| 6,007,509 A | 12/1999 | Kingsley et al. |
| 6,019,742 A | 2/2000 | Headley et al. |
| 6,027,441 A | 2/2000 | Cantu et al. |
| 6,039,711 A | 3/2000 | Headley et al. |
| 6,060,022 A | 5/2000 | Pang et al. |
| 6,074,335 A | 6/2000 | Headley et al. |
| 6,099,491 A | 8/2000 | Headley et al. |
| 6,102,883 A | 8/2000 | Kingsley et al. |
| 6,168,561 B1 | 1/2001 | Cantu et al. |
| 6,251,291 B1 | 6/2001 | Lamphere et al. |
| 6,254,784 B1 | 7/2001 | Nayak et al. |
| 6,258,577 B1 * | 7/2001 | Goodrich et al. .......... 435/173.3 |
| 6,261,217 B1 | 7/2001 | Unger et al. |
| 6,296,602 B1 | 10/2001 | Headley et al. |
| 6,315,706 B1 | 11/2001 | Unger et al. |
| 6,348,031 B1 | 2/2002 | Unger et al. |
| 6,348,156 B1 | 2/2002 | Vishnoi et al. |
| 6,398,760 B1 | 6/2002 | Danby |
| 6,413,200 B1 | 7/2002 | Jorgensen et al. |
| 6,524,231 B1 | 2/2003 | Westberg et al. |
| 6,582,349 B1 | 6/2003 | Cantu et al. |
| 6,585,499 B2 | 7/2003 | Nguyen et al. |
| 6,602,179 B1 | 8/2003 | Headley et al. |
| 6,605,223 B2 | 8/2003 | Jorgensen et al. |
| 6,652,475 B1 | 11/2003 | Sahines et al. |
| 6,666,665 B1 | 12/2003 | Nguyen et al. |
| 6,733,433 B1 | 5/2004 | Fell |
| 6,827,863 B2 | 12/2004 | Doleck et al. |
| 6,852,074 B1 | 2/2005 | Jorgensen et al. |
| 2002/0082153 A1 | 6/2002 | Jorgensen et al. |
| 2003/0191005 A1 | 10/2003 | Coelho et al. |
| 2003/0194104 A1 | 10/2003 | Irby et al. |
| 2003/0195104 A1 | 10/2003 | Hlavinka et al. |
| 2003/0211927 A1 | 11/2003 | Cantu et al. |
| 2004/0104182 A1 | 6/2004 | Holmes et al. |
| 2006/0205581 A1 | 9/2006 | Chammas |

FOREIGN PATENT DOCUMENTS

| | | |
|---|---|---|
| EP | 0014093 | 5/1983 |
| EP | 0350495 | 8/1992 |
| EP | 0536594 | 4/1993 |
| EP | 0235160 | 6/1994 |
| EP | 0587257 | 6/1998 |
| EP | 0578086 | 8/2001 |
| EP | 1208856 | 5/2002 |
| EP | 1757318 | 2/2007 |
| NL | 1008210 | 2/1998 |
| WO | WO92/00145 | 1/1992 |
| WO | WO00/54823 | 9/2000 |
| WO | WO00/54824 | 9/2000 |
| WO | WO03/026802 | 4/2003 |
| WO | WO03/089027 | 10/2003 |
| WO | WO2007/001754 | 1/2007 |

* cited by examiner

PMCA 1st round

PMCA 2nd round

METHODS FOR WASHING A RED BLOOD CELL COMPONENT AND FOR REMOVING PRIONS THEREFROM

This application claims the priority of U.S. Provisional Application 60/853,397 filed on Oct. 20, 2006.

The United States Government has certain rights in this invention pursuant to grant number W81XWH-05-2-0001 awarded by the United States Department of Defense.

FIELD OF INVENTION

The present invention relates to an apparatus and a method for washing multiple units of a red blood cell component in a balanced centrifuge.

BACKGROUND OF INVENTION

An apparatus for processing blood components is known from document WO 03/089027. This document describes a centrifuge adapted to cooperate with an annular separation bag connected to at least one product bag, e.g. a platelet component bag. The centrifuge includes a rotor having a turntable for supporting the separation bag, a central compartment for containing the product bag connected to the separation bag; and a squeezing system for squeezing the separation bag and causing the transfer of a separated component (e.g. platelets suspended in plasma) from the separation bag into the product bag. The centrifuge of this apparatus processes one composite fluid or unit of whole blood at a time.

Also, an apparatus for separating or processing multiple volumes of blood in a balanced centrifuge is known from the publication WO2007/001754 or PCT/U.S. 2006/21827.

SUMMARY OF INVENTION

One object of the instant invention is to wash multiple individual units of blood components or blood products simultaneously using a single balanced centrifuge.

Another object of the instant invention is to process blood components or blood products to remove any prions contained therein or to reduce the amount of pathogens contained therein.

The invention relates to a method of washing multiple units of blood product wherein the method includes the steps of adding washing solution to each unit of blood product; placing each unit of blood product into a separate washing cell of a centrifuge having a plurality of rotating cells; rotating the centrifuge to sediment the blood product from supernatant including the washing solution; balancing the centrifuge to accommodate for any variations in the washing cells; and transferring the supernatant from the washing cell to leave washed blood product in the washing cell. The blood product can be an already separated blood component such as red blood cells or whole blood can be collected and separated into components prior to washing of the desired component.

The invention further relates to a method of reducing proteins in a blood product that includes the steps of collecting a plurality of units of blood product; mixing each unit of blood product with washing solution; simultaneously centrifuging the plurality of units of blood product with washing solution; and removing the resulting supernatant including any proteins and wash solution from the centrifuging units. The proteins to be removed can include prion proteins. Also pathogens may be removed to reduce the resulting pathogen amount in the collected blood product. The collected blood product for prion and/or pathogen removal includes red blood cells separated from collected whole blood or a collected red blood cell product.

The invention additionally relates to a method of washing multiple units of blood product wherein the method includes adding washing solution to each unit of blood product; providing a centrifuge having a plurality of washing cells; placing each unit of blood product into a separate washing cell of the centrifuge; rotating the centrifuge to sediment the blood product from supernatant including the washing solution; and transferring, during the rotating step, the supernatant from the washing cell to leave washed blood product in the washing cell.

DETAILED DESCRIPTION

Figure 1:
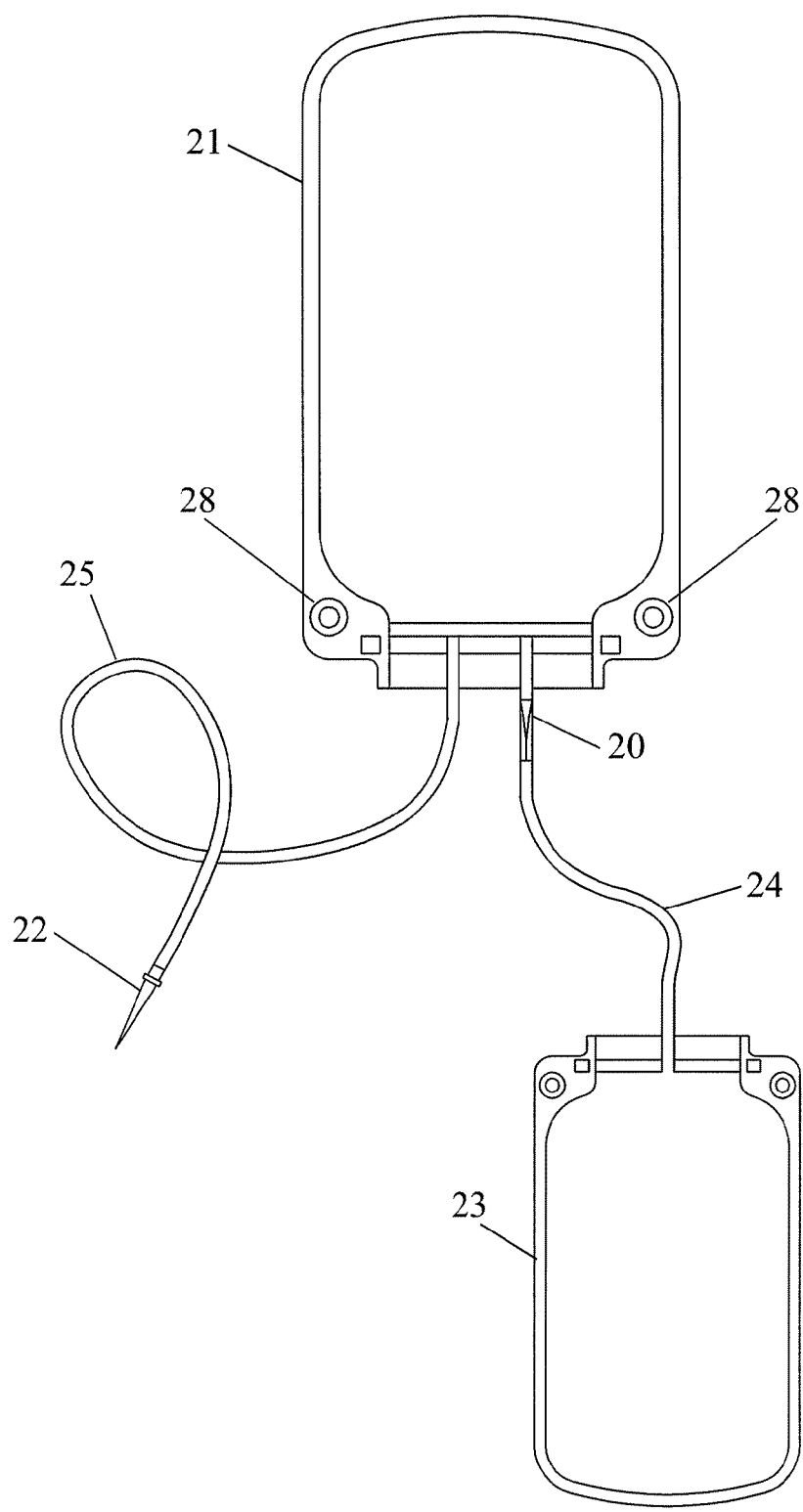
FIG. 1 is a schematic view of a bag set for use with a centrifuge in accordance with the instant invention.

FIG. 1 shows an example bag set for use with either centrifuge 40, 200, or 130 as described below. The bag set includes flexible wash bag 21 that is generally flat and rectangular. It is made of two rectangular sheets of plastic material that are welded together so as to define there between an interior space having a main rectangular portion. A first tube or conduit 24 is connected to the main rectangular portion, and a second tube or conduit 25 is also connected to bag 21. The location of the connection of tubes 24 and 25 to the wash bag 21 can vary. The proximal ends of the tubes 24 and 25 may be embedded between the two sheets of plastic material so as to be parallel or they may be attached to bag 21 through ports. The wash bag 21 further comprises a hole 28 in each of its corners that may be adjacent to the tubes 24 and 25. The holes 28 are used to secure the wash bag 21 to a wash cell, as will be described later.

The wash bag 21 initially contains a volume of cell product to be washed, and as described below, the cell product is a red blood cell product though it is understood that other products or components, such as platelets, could be washed using the principals of the invention.

The second tube 25 is a washing liquid tube having a needle or spike 22 connected to its distal end. Prior to the initiation of the wash cycle, the needle 22 or spike is inserted into a bag of wash solution (not shown) and the wash solution flows into the wash bag 21. After a desired volume of wash solution has entered the wash bag 21, the wash solution tube 25 is sealed and cut. The wash solution is added to the wash bag 21 prior to insertion of the bag into a centrifuge.

The first satellite bag 23 is intended for receiving washing solution or supernatant after use. It is flat and substantially rectangular. It is connected to the distal end of the first tube 24. First tube 24 further includes an optional breakable stopper or frangible connector 20 for blocking flow therethrough.

In an alternative embodiment bag 23 may initially contain the wash solution. Thus the solution containing bag 23 may be attached to the wash bag 21 of the bag set of FIG. 1 by known sterile docking methods or techniques (not shown). A frangible connector, breakable stopper or other clamp or valve may then be opened to transfer the wash solution from bag 23 to the wash bag 21 prior to insertion into the centrifuge. The same satellite bag 23 may then receive the washing solution or supernatant after use. Alternatively wash solution may be contained in the wash bag 21 prior to introduction of the blood product.

Figure 2:
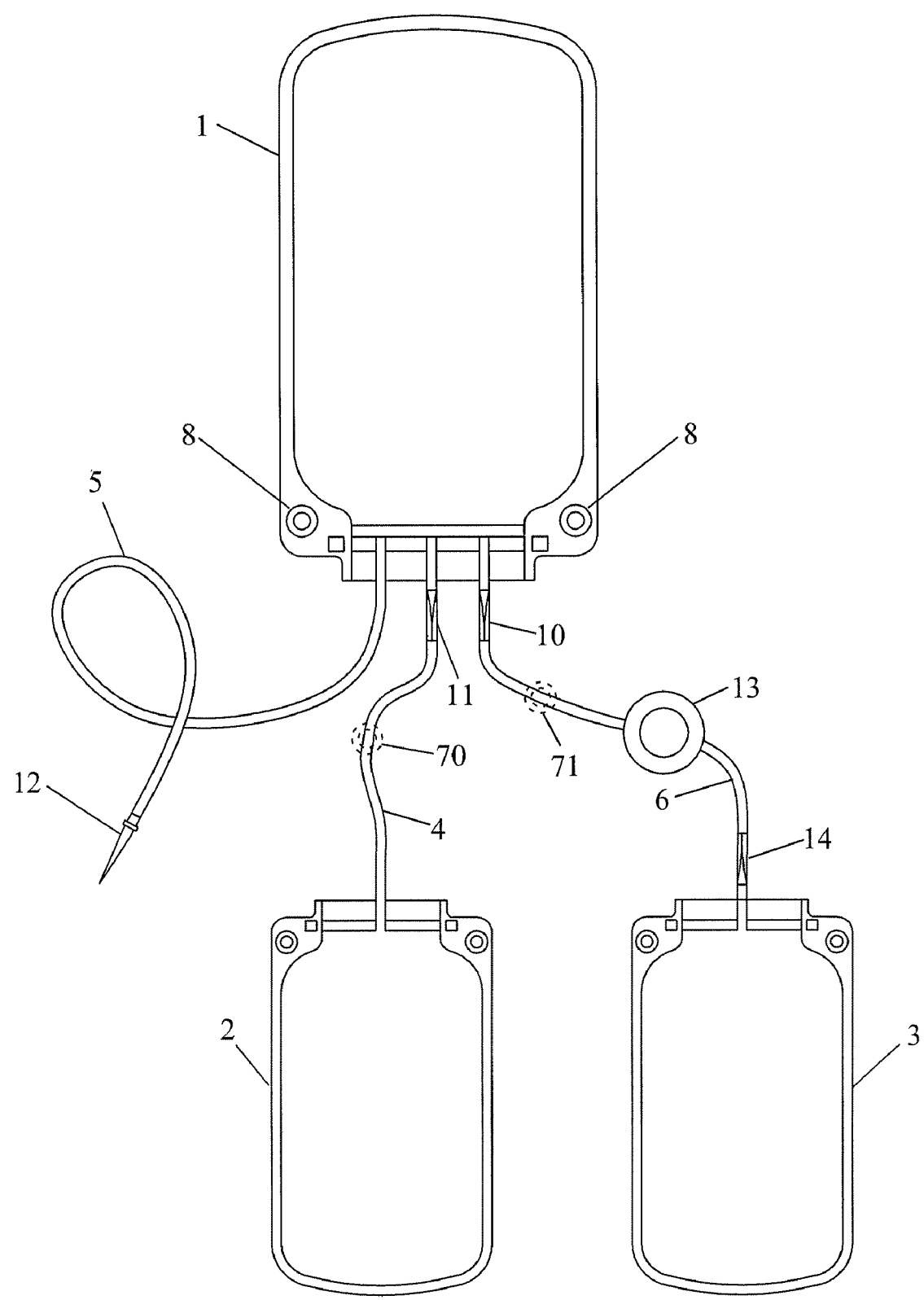
FIG. 2 is a schematic view of a second bag set with filter for use with a centrifuge in accordance with the instant invention.

FIG. 2 shows an example of a bag set that is similar to FIG. 1 in that it includes wash bag 1, conduits or tubes 5 and 4, spike or needle 12, optional breakable stopper or frangible 11, and satellite bag 2. The wash bag 1 further includes a hole 8 in each of its corners adjacent to the tubes 4 and 5. The set further includes second satellite bag 3 that is flat and substantially rectangular. Bag 3 is connected to the distal end of third tube or conduit 6. The third tube 6 comprises two segments connected to a leuko-reduction filter 13. The third tube 6 is also connected to wash bag 1 and is fitted with optional breakable stopper or frangible 10 for blocking flow therethrough. The third tube also has second optional breakable stopper 14 proximate to satellite bag 3. In this embodiment bag 2 can also initially contain the wash solution and be sterile docked to wash bag 1. After washing the same satellite bag 2 may receive the supernatant.

Figure 3:
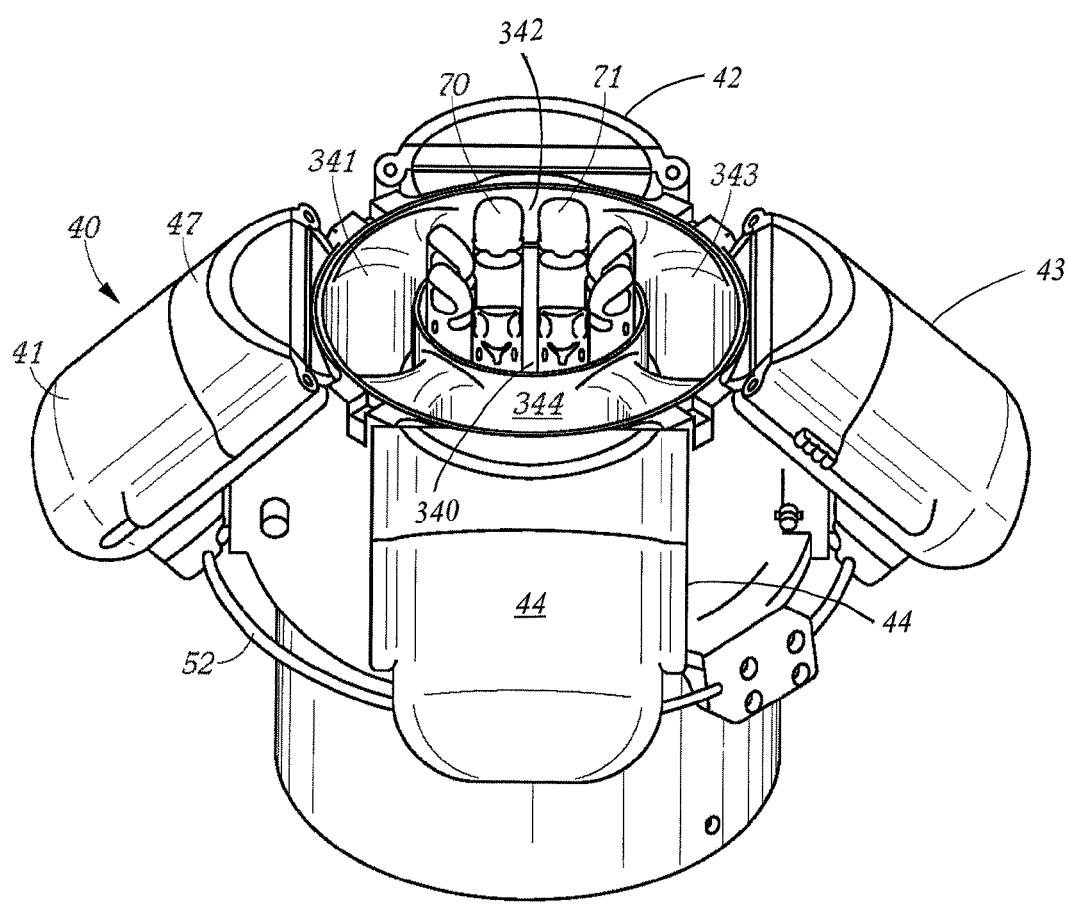
FIG. 3 is a perspective view of a rotor of a washing apparatus.
Figure 4:
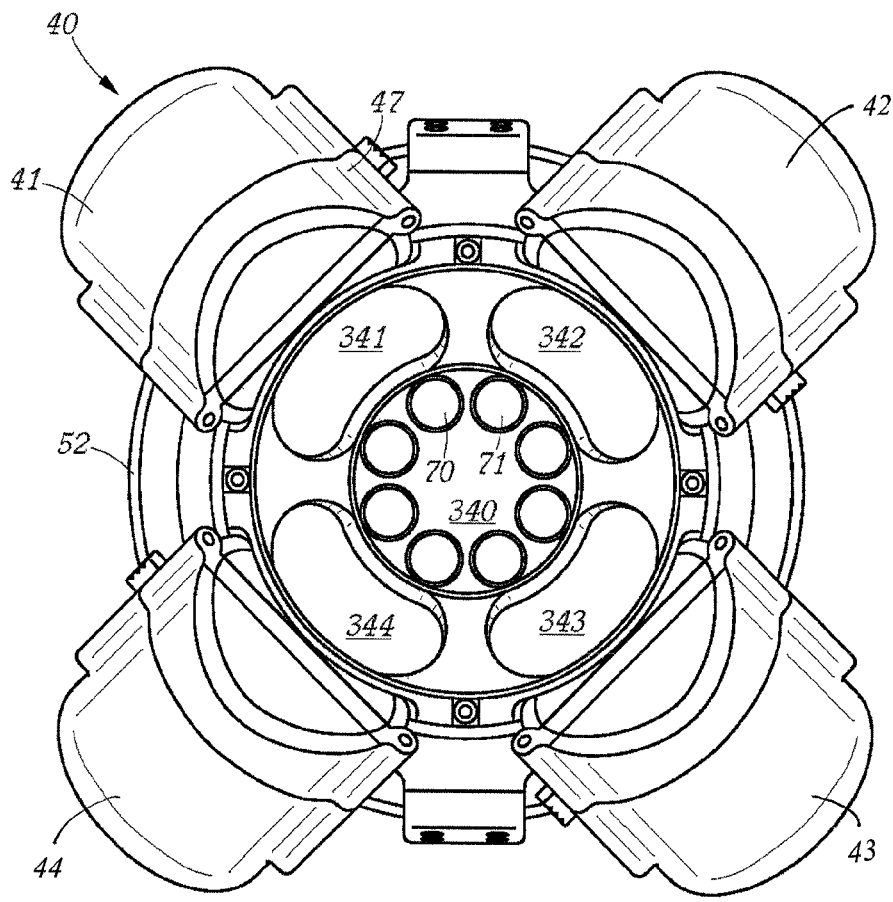
FIG. 4 is a top view of the rotor of FIG. 3.
Figure 6:
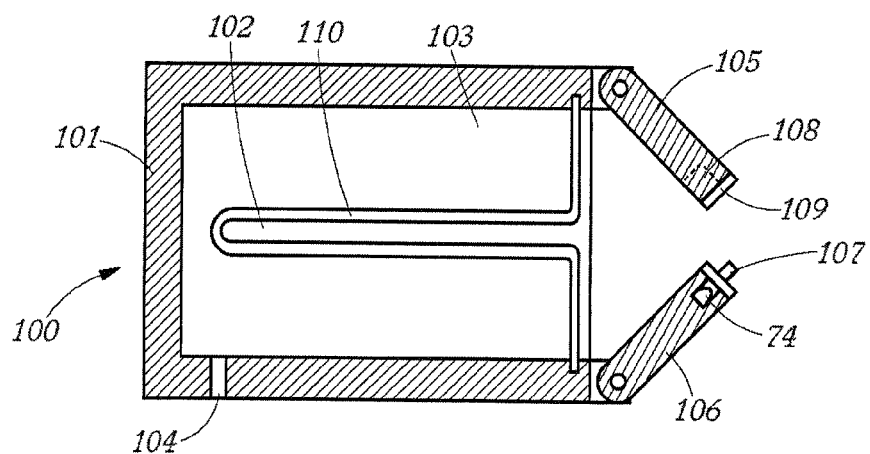
FIG. 6 is a schematic view, in cross-section along a radial plane, of a washing cell of the washing apparatus of FIG. 5.

FIGS. 3 and 4 show a centrifuge 40 of a centrifugal washing apparatus.

Figure 5:
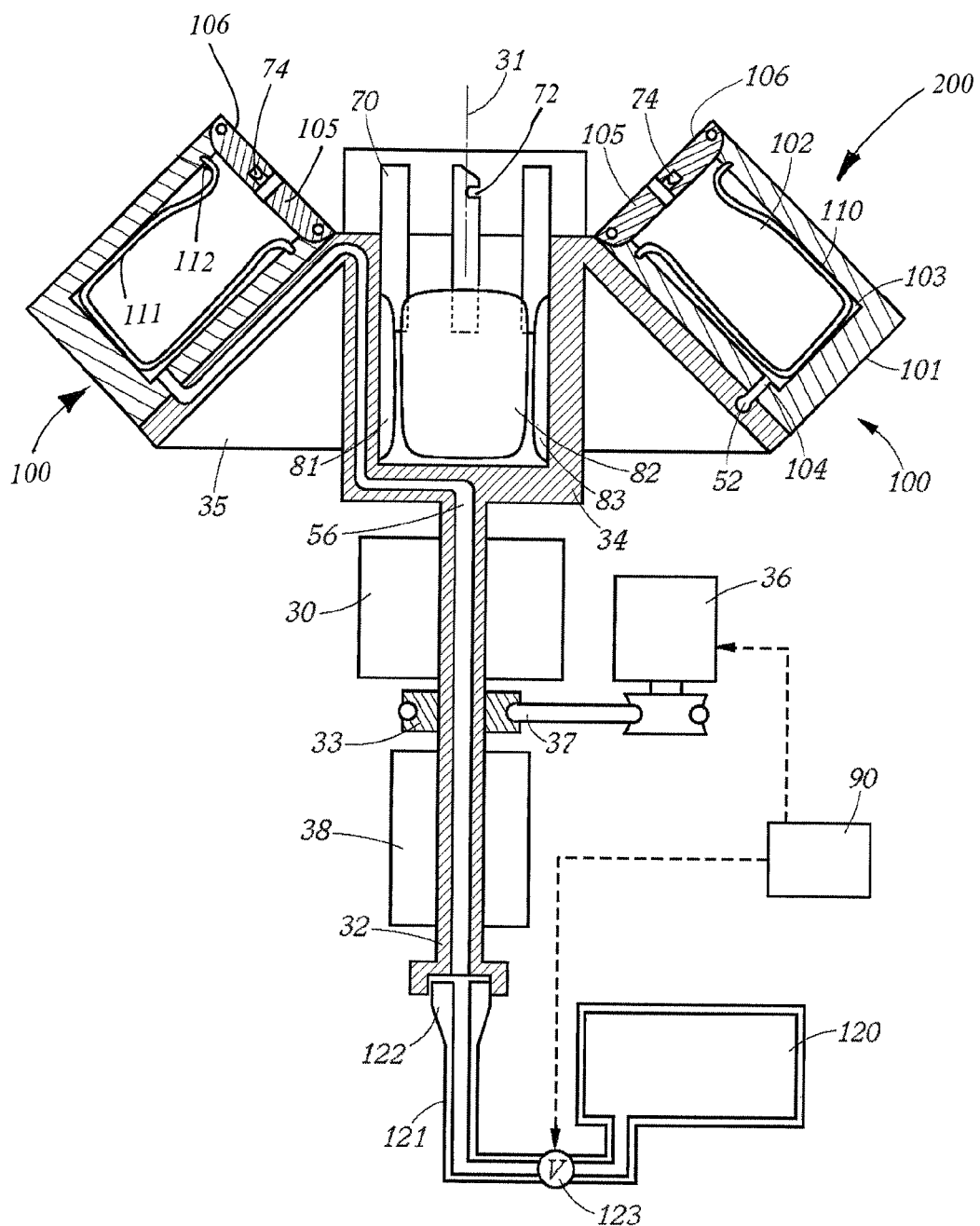
FIG. 5 is a schematic view, in cross-section along a diametric plane, of an alternative rotor of a washing apparatus.

The centrifuge of this embodiment comprises four satellite cavities 341, 342, 343, 344 that are arranged around or may form part of a central cylindrical cavity 340, in which four pairs of pinch valve members 70, 71 are mounted with their longitudinal axes parallel to the rotation axis 31 (see second embodiment, FIG. 5). Each cavity 341, 342, 343, 344 has a regular bean-like cross-section, and a central longitudinal axis that is parallel to the rotation axis 31 and intersects the longitudinal axis of the associated washing cell 41, 42, 43, 44. Although the cavities 341, 342, 343, and 344 are shown as having bean like cross sections it is understood that other shapes could also be utilized.

The centrifuge 40 is adapted to hold satellite bags (2, or 23, and optionally 3) in the cavities 341, 342, 343, and 344. The cavities 341, 342, 343, and 344 may also contain fixed or removable containers for receiving the satellite bags.

The centrifuge, as shown in FIG. 3, also includes four washing cells 41, 42, 43, and 44. Each of these washing cells is adapted to receiving a washing bag or container 1 or 21 of bag set of FIG. 2 or 1. The washing cells 41, 42, 43, and 44 may have a hingeable top portion 47 for providing access to the cell. Alternatively as shown in FIG. 5, a removable top cover, such as 105, 106 may also be provided for access. Any top cover should have a slot for accommodating tubing or conduit 4 or 24 and, optionally tubing 6.

Although four washing cells 41, 42, 43, 44 and associated satellite bag cavities, 341, 342, 343, 344, are shown, it is understood that only two opposing cavities and cells, (41, 341 and 43, 343), for example, could also be provided. Similarly the number of washing cells and satellite cavity sets can be increased to six or beyond depending on the size of the centrifuge.

Also, although pairs of valve elements 70 and 71 are shown it is understood that for the bag set of FIG. 1, only one valve element per wash cell 41, 42, 43, 44 need be provided.

For the embodiments of FIGS. 3, 4, and 5, (the washing cells 100 of the centrifuge 200 are described below), the centrifuge includes a rotor that is supported by a bearing assembly 30 allowing the rotor to rotate around a rotation axis 31. The rotor includes a cylindrical rotor shaft 32 to which a pulley 33 is connected; a central cylindrical container 34 or 340 (FIGS. 3, 4 and 5) which is connected to the rotor shaft 32 at the upper end thereof so that the longitudinal axis of the rotor shaft 32 and the longitudinal axis of the container 34 or 340 coincide with the rotation axis 31, and a frusto-conical turntable 35 connected to the upper part of the central container 34 or 340 so that its central axis coincides with the rotation axis 31. The frusto-conical turntable 35 flares underneath the opening of the container 34 or 340. The four identical washing cells 41, 42, 43, and 44 of the embodiment of FIGS. 3 and 4 or the washing cells 100 as shown in of FIG. 5 are attached to the turntable.

The centrifuge 200 and the centrifuge 40 further include a motor 36 coupled to the rotor by a belt 37 engaged in a groove of the pulley 33 so as to rotate the rotor about the rotation axis 31.

The embodiment of FIGS. 5-10 show a washing cell 100. In this embodiment washing cell 100 includes a container 101 having the general designed shape of a rectangular parallelepiped. The washing container 101 (also referred to as the "washing compartment") of the cell 100 is so dimensioned as to loosely accommodate a washing bag 21 or 1 full of liquid, of the type shown in FIGS. 1 and 2. The washing cell 100 further comprises an elastic diaphragm 110, which defines within the cavity of the container 101, a first chamber 102 for receiving a washing bag 1 or 21, and a second hydraulic chamber 103 that is connected to the peripheral manifold 52 (see FIGS. 3 and 4), through an inlet aperture 104 close to the bottom of the container 101. The washing cell 100 further comprises a lid having two flaps 105, 106 that are hinged to the longer parallel sides of the opening of the container 101. The two flaps 105, 106 can be locked in a closed position by a locking means (not shown). The washing cell 100 further comprises a securing means for securing a washing bag 1 within the washing cell 100. The bag securing means comprises two pins 107 and two corresponding recesses 108 that respectively protrude or open on the edges of the flaps 105, 106 that face each other when the lid is closed. The two pins 107 are so spaced apart and dimensioned as to fit into the two holes 8 or 28 in the upper corner of a wash bag 1 or 21. The two flaps 105, 106 also comprise on their facing edges semi-cylindrical holes 109 for accommodating the proximal end of three tubes 4, 6 or tube 24 embedded in the upper area of a wash bag 1 or 21. Two holes may be optionally provided for the bag set of FIG. 2 while one hole may be provided for the bag set of FIG. 1. An outer flap 106 includes a cavity facing the median semi-cylindrical hole 109, for containing the tube sensor 74.

The washing cells 100, or 41, 42, 43, and 44 are mounted on the turntable 35 so that their respective median longitudinal axes intersect the rotation axis 31, so that they are located substantially at the same distance from the rotation axis 31, and so that the angles between their median longitudinal axes are substantially the same (i.e. 90 degrees). The exact position of the washing cells 100, or 41, 42, 43, and 44 on the turntable 35 is adjusted so that the weight on the turntable is equally distributed when the washing cells 100, or 41, 42, 43, and 44 are empty, i.e. so that the rotor is balanced. Due to the arrangement of the washing cells 100 or 41, 42, 43, and 44 on the turntable 35 such cells are inclined with respect to the rotation axis 31 of an acute angle equal to the angle of the frustum of a cone that geometrically defines the turntable 35.

The centrifuge of FIG. 5 differs from the centrifuge of FIGS. 3 and 4 with respect to the shape of the washing cell 100 and also in that the central compartment 340 is a single compartment without separate cavities 341, 342, 343, and 344. It is understood that the centrifuge of FIG. 5 can have multiple washing cells 100 including four and six in number although only two are shown.

Figure 7:
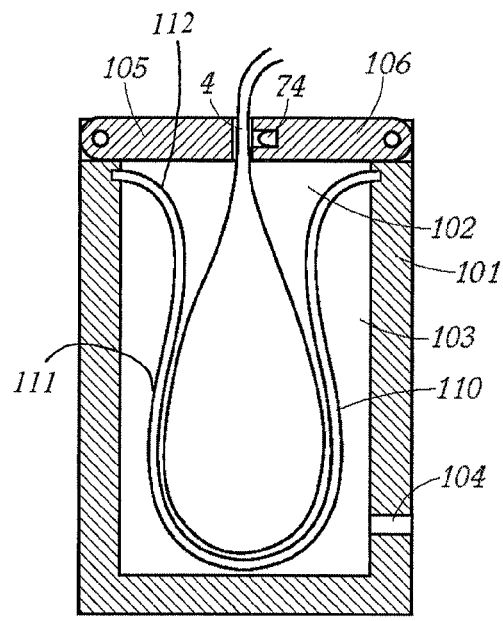
FIGS. 7-9 are schematic views, in cross-section along a radial plane, of the washing cell of FIG. 6 containing a washing bag at different stages of a washing process.
Figure 8:
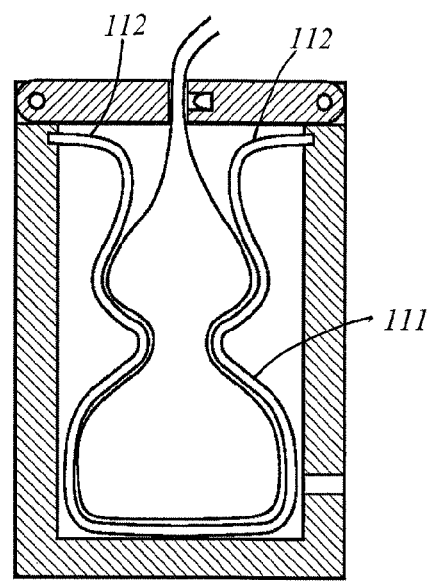
Figure 9:
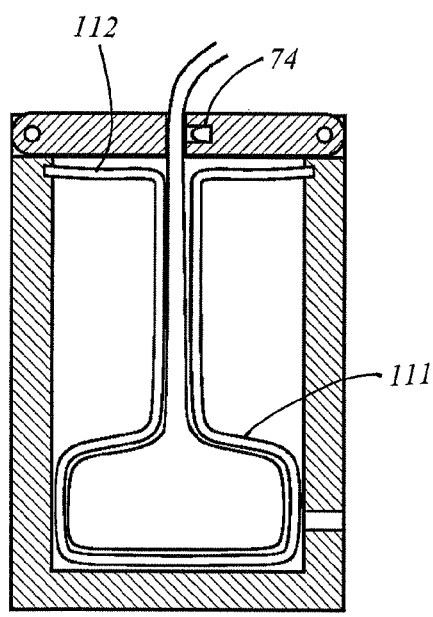

As shown in FIGS. 6 to 9, the diaphragm 110 comprises a flat rectangular socket 111 almost as wide as a washing cell 100. The diaphragm 110 further comprises a large, rectangular, connecting portion 112 extending around the mouth of the socket 111, perpendicularly to the socket 111 when the diaphragm 110 is not deformed by a wash bag 1 and it is held in an upright position (FIGS. 5 and 7). The socket 111 is connected to the connecting portion 112 along the longitudinal median axis thereof. The connecting portion 112 has a surface slightly larger than a transversal cross-section of the cavity of the container 101. The diaphragm 110 is tightly attached to the top of the container 101 by a peripheral area of the connecting portion 112. The diaphragm 110 is made of an elastic and deformable elastomeric material so selected that the diaphragm 110 conforms very closely to the shape of a wash bag 1 or 21 before and during centrifugation and as shown in FIGS. 7 to 9.

The washing apparatus further comprises a transferring mechanism for transferring supernatant and optionally washed cells into a satellite bag 2 or 23 connected thereto. The transferring mechanism comprises a squeezing system for squeezing washing bag 21 or 1 within the washing compartment or cells 41, 42, 43, 44 or 100 for causing the transfer of supernatant including any remaining plasma, cells and wash solution into the satellite bag. The transferring mechanism will be described with respect to cell 100 though it is understood that the operation and structure is the same for cells 41, 42, 43, and 44.

As shown in FIG. 5 the transferring mechanism includes a reservoir 120 for hydraulic liquid, which is fixed with respect to the rotor, and which is directly connected to the rotor duct 56 by a conduit 121 and a rotary seal 122. The conduit 121 is fitted with a valve 123. The reservoir 120 is secured to a frame of the washing apparatus so as to be lower than the four washing cells 100. When the washing apparatus is used for washing red blood cells and then separating the supernatant, the density of the hydraulic liquid is selected so as to be between the density of packed red blood cells and the supernatant which may include saline, plasma and any other cells.

The transferring mechanism includes the reservoir 120 that is directly connected to the rotor duct 56 by the rotary seal 122, the hydraulic chambers 103, and the motor 36 that drives the rotor in rotation. When the valve 123 is opened and the rotation speed of the rotor reaches a determined threshold, which depends on the height between the reservoir 120 and the washing cells 100 and the distance between the rotation axis 31 and the washing cells 100, then the hydraulic liquid flows from the reservoir 120 into the hydraulic chambers 103 so as to fill up the hydraulic chamber 103 and squeeze the wash bag 1 or 21 therein, whatever the volume/weight of the wash bag 1 or 21. The speed threshold is substantially below the rotation speed at which the rotor is rotated for separating the supernatant from the red blood cells as described below. The transfer of the supernatant from the wash bag 21 or 1 into a satellite bag 23 or 2 is then controlled by the opening/closing of the pinch valve member 70 (described below) in which the tube 4 or 24 connecting the two bags is inserted.

As the apparatus of the instant invention can be used to wash multiple bags of red blood cells in multiple wash bags and cells and since the starting red blood cell product can vary in weight and volume as well as hematocrit, the washing apparatus thus includes a balancing mechanism which includes the reservoir 120 that is directly connected to the rotor duct 56 through the rotary seal 122, the hydraulic chambers 103, the interconnecting tubing 52 between the chambers, the motor 36 that drives the rotor in rotation, and the valve 123. At the onset of a separation process, the valve 123 is opened for a predetermined period of time so as to allow the transfer, in the interconnected hydraulic chambers 103, of a volume of hydraulic liquid sufficient to fill container 101. With all containers 101 full of fluid (hydraulic and wash solution) the rotor comes into balance even in the most unbalanced situation. This balancing volume takes into account the maximum difference in volume between two starting products A variant of the washing apparatus eliminates the valve 123 on the conduit 121 connecting the reservoir 120 to the rotor duct 56. As a result, when the threshold speed is reached, the hydraulic liquid is pumped from the reservoir 120 into the hydraulic chambers 103 until the pressure that is building up within the washing cells 100 prevents further pumping.

The washing apparatus further comprises four pairs of a first and second pinch valve members 70, 71 that are mounted on the rotor around the opening of the central container 34 or 340. Although four pairs of pinch valve members are shown in the figures it is understood that if only the bag set of FIG. 1 is used without further transfer of the red blood cell product, then only one pinch valve for each associated washing cell is necessary. For the purposes of this explanation the washing apparatus will be described with pairs of pinch valve member.

Each pair of pinch valve members 70, 71 faces one washing cell 41, 42, 43, 44 or 100, with which it is associated. The pinch valve members 70, 71 are designed for selectively blocking or allowing a flow of liquid through a flexible plastic tube, and selectively sealing and cutting the plastic tube. Each pinch valve member 70, 71 comprises an elongated cylindrical body and a head having a groove 72 (FIG. 5) that is defined by a stationary upper jaw and a lower jaw movable between an open and a closed position. The groove 72 is so dimensioned that one of the tubes 4, 6 or 24 of the bag sets shown in FIGS. 1 and 2 can be snuggly engaged therein when the lower jaw is in the open position. The elongated body contains a mechanism for moving the lower jaw and it is connected to a radio frequency generator that supplies the energy necessary for sealing and cutting a plastic tube. The pinch valve members 70, 71 are mounted inside the central container 340 or 34 adjacent the interior surface thereof, so that their longitudinal axes are parallel to the rotation axis 31 and their heads protrude above the rim of the container 340 or 34. The position of the pair of pinch valve members 70, 71 with respect to a wash bag 1 and the tubes 4 and 6 connected thereto when the wash bag 1 rests in the washing cell 41, 42, 43, 44 is shown in dotted lines in FIG. 2. Electric power is supplied to the pinch valve members 70, 71 through a slip ring array 38 that is mounted around a lower portion of the rotor shaft 32.

The washing apparatus further comprises four sensors 74 for monitoring the movement of the supernatant or blood component occurring within each wash bag 1 or 21 when the apparatus operates. Each sensor 74 is embedded in the lid 47, 105, 106 of the washing cells 41, 42, 43, 44 or 100. When a wash bag 1 or 21 rests in the container 41, 42, 43, 44 or 100 and the lid 47 or 105, 106 is closed, the sensor 74 (later the tube sensor) faces the proximal end of the first tube 4 or 25. The tube sensor 74 is able to detect the presence or absence of liquid in the tube 4 or 24 as well as to detect blood cells in a liquid. Each sensor 74 may comprise a photocell including an infrared LED and a photo-detector. Electric power is supplied to the sensor 74 through the slip ring array 38 that is mounted around the lower portion of the rotor shaft 32.

The washing apparatus may also optionally include a second balancing mechanism, for balancing the rotor when the weights of the supernatant transferred into the satellite bags 2 or 23 in the central container 34 or 340 are different. For example, when two starting red blood cell components have the same hematocrit and different volumes, the volumes of any plasma extracted with the supernatant from each donation are different, and the same is true when two starting components have the same volume and different hematocrit. As shown in FIG. 5, the second balancing mechanism comprises four flexible rectangular pouches 81, 82, 83 and a fourth pouch opposite pouch 82 that are interconnected by four tube sections (not shown), each tube section connecting two adjacent pouches by the bottom thereof. The pouches 81, 82, 83 and fourth pouch contain a volume of balancing liquid having a density close to the density of the starting red blood cell mixture. The volume of balancing liquid is so selected as to balance the rotor in the most unbalanced situation. The four pouches 81, 82, 83 and fourth pouch are so dimensioned as to line the inner surface of the central container 34 or 340 and to have an internal volume that is larger than the volume of balancing liquid so that the balancing liquid can freely expand in any of the pouches 81, 82, 83, or the fourth pouch. In operation, if, for example, four satellite bags 2 respectively adjacent to the four pouches 81, 82, 83, and the fourth pouch receive different volumes of a supernatant, the four satellite bags 2 will press unevenly, under centrifugation forces, against the four pouches 81, 82, 83, fourth pouch, which will result in the balancing liquid becoming unevenly distributed in the four pouches 81, 82, 83, fourth pouch and compensating for the difference in weight in the satellite bags 2.

The washing apparatus further comprises a controller 90 including a control unit (e.g. a microprocessor) and a memory unit for providing the microprocessor with information and programmed instructions relative to various washing protocols as described below and to the operation of the apparatus in accordance with such washing protocols. In particular, the microprocessor is programmed for receiving information relative to the centrifugation speed(s) at which the rotor is to be rotated during the various stages of the washing process and information relative to the various transfer flow rates at which supernatant and/or components are to be transferred from the washing bag 1, 21 into the satellite bags 2 or 23. The information relative to the various transfer flow rates can be expressed, for example, as hydraulic liquid flow rates in the hydraulic circuit. The microprocessor is further programmed for receiving, directly or through the memory, information from the four photocells or sensors 74 for controlling the centrifuge motor 36. It further receives and transmits information about the valve 123 and the four pairs of pinch valve members 70, 71 so as to cause the washing apparatus to operate along a selected washing protocol.

Instead of the centralized hydraulic squeezing system described above, a washing apparatus can be fitted with as many independent squeezing means as washing cells 100. An independent squeezing means may be comprised, for example, of a plate that can be moved by any electro-magnetic, electro-mechanical or hydraulic mechanism so as to squeeze a wash bag against a wall of the cavity 102 of the container 101 of a washing cell 100.

Instead of a system of interconnected hydraulic chambers or pouches, the first and/or second balancing means can comprise a ball balancer including a circular cage in which heavy balls can move freely. The circular cage is mounted on the rotor so as to be centered on the rotation axis 31.

Figure 10:
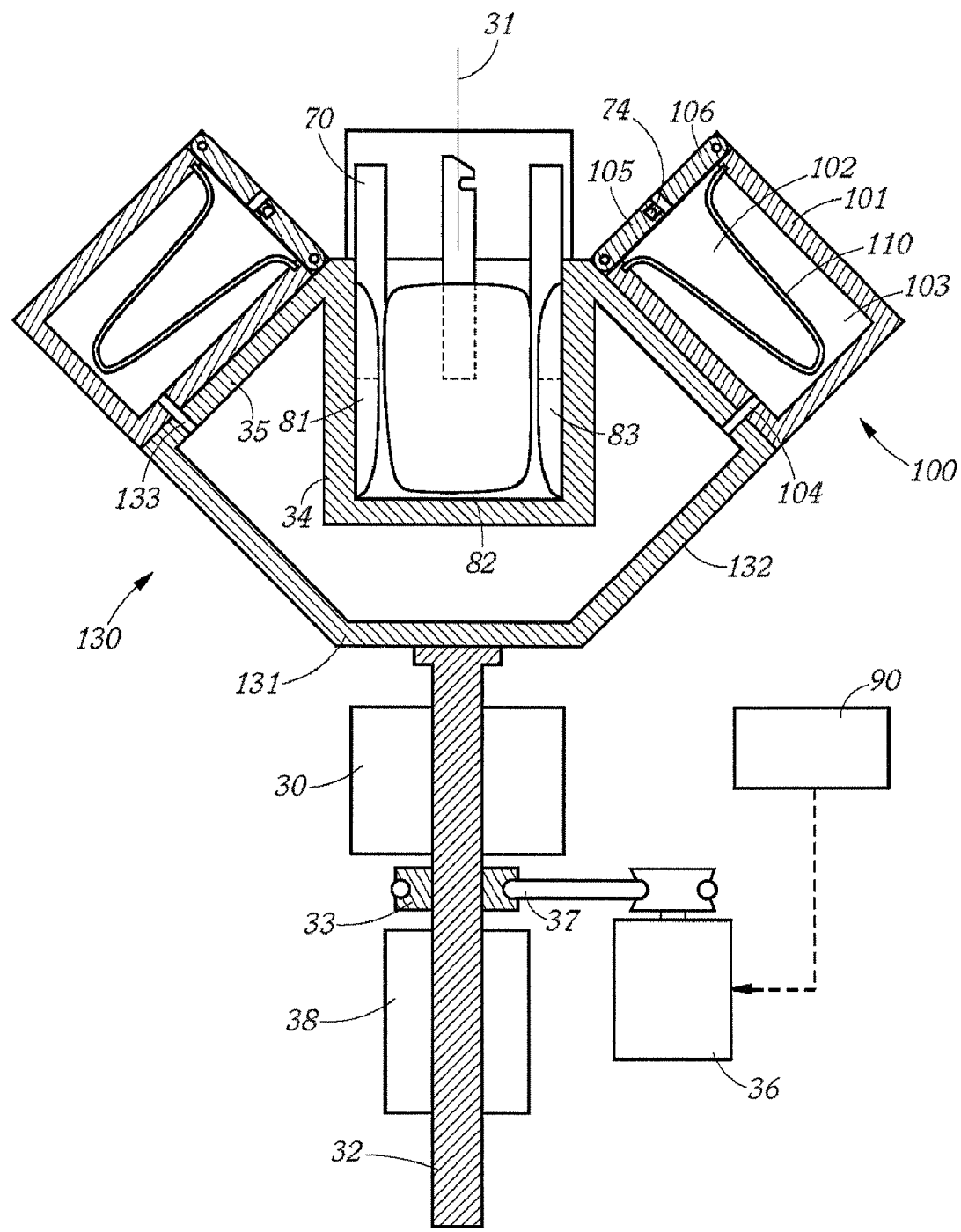
FIG. 10 is a schematic view, in cross-section along a diametric plane, of a third embodiment of a washing apparatus.

FIG. 10 shows an alternative embodiment of a washing apparatus for four discrete volumes of a red blood cell component.

The alternative washing apparatus does not comprise a fixed reservoir directly connected to the washing chambers, via a conduit, a rotary seal and a rotor duct. Also, the alternative washing apparatus includes a hydraulic liquid reservoir 130 that is mounted on the rotor.

The rotor of the apparatus of FIG. 10 includes a central container 34 for satellite bags, having the shape of a cylindrical bucket and a turntable 35 having a frusto-conical wall supporting four washing cells 100 at an angle with respect to the rotation axis 31. The turntable 35 is connected by its smaller diameter section to an upper rim of the central container 34 so as to flare underneath the rim of the central container 34. A reservoir 130 for hydraulic liquid is provided which includes a circular bottom wall 131 and frusto-conical wall 132 connected by its smaller diameter section to the circular bottom wall 131 and by its larger diameter section to the lower rim of the turntable 35 (i.e. the section of the turntable having the larger diameter). In other words, the interior of the reservoir 130 has a complex geometrical volume that is symmetrical with respect to the rotation axis 31 and that is defined by the outside surface of the central container 34, the inner surface of the turntable 35, the inner surface of the frusto-conical wall 132 of the reservoir, and the inner surface of the bottom wall 131 of the reservoir, and a rotor shaft 32, which is connected to the bottom wall of the reservoir 130.

The reservoir 130 is fluidly connected to the hydraulic chamber 103 of each washing cell 100 by an outlet aperture 133 through the turntable 35 that coincides with the inlet aperture 104 of the hydraulic chambers 103. As shown, the outlet apertures 133 are located the farthest from the rotation axis 31. With this arrangement, the hydraulic liquid flows from the reservoir 130 into the hydraulic chambers 103 of the washing cells 100 under centrifugal forces as soon as the rotor starts rotating. The density of the hydraulic fluid is selected so as to be between the density of packed red cells and the density of the washing solution.

In this embodiment of the washing apparatus, the transferring mechanism essentially comprises the reservoir 130, the hydraulic chambers 103 and the motor 36 that drives the rotor in rotation. When the rotor rotates, the hydraulic liquid drains from the reservoir 130 into the hydraulic chambers 103 under centrifugal forces and presses the wash bag 1 or 21 within the washing cell 100 through the elastic diaphragm 110. The transfer of supernatant or component from a wash bag 1 or 21 into a satellite bag 2 or 23 is controlled by the opening/closing of the pinch valve member 70 in which the tube 4 or 24 connecting the two bags is inserted.

The first balancing mechanism essentially comprises the reservoir 130, the hydraulic chambers 103 and the motor 36 that drives the rotor in rotation. As soon as the rotor starts rotating, hydraulic fluid flows from the reservoir 130 into the hydraulic chambers 103 until it completely fills up the space left vacant in the washing cells 100 by the wash bag 1 or 21, which happens before the rotor has reached the desired sedimentation speed.

The method of washing cells utilizing the washing apparatus described above is as follows.

The cells to be washed may have been separated in a centrifugal separator such as that described in WO/2007/001754. This separation apparatus has a number of features in common with the instant washing apparatus allowing the separator to be used for washing after separation following the below described protocol.

Alternatively cells may separated from whole blood or other blood components utilizing any known cell separators including apheresis equipment or a centrifuge for separating multiple bags of whole blood.

When cell separation or apheresis equipment is used, the initial starting product is a cell component, such as red blood cells, from which a significant amount of the plasma has been removed. For the remainder of the washing protocol the description will refer to a red blood cell component though it is understood that other components or products could also be washed.

The starting red blood cell component is in wash bag 1 or 21 depending on the bag set used. For the purpose of the rest of the washing description only the bag set of FIG. 2 will be described though it is understood the bag set of FIG. 1 would be used if no leuko-reduction was desired and if there was further processing before storage. Wash fluid such as saline is provided through tubing line 5. Alternatively the red blood cells can be collected from the separation apparatus into wash bag 1 already containing the wash solution. The wash solution and the red blood cells are manually mixed in the wash bag 1.

After the wash bag 1 contains the red blood cells and wash solution, the bag set can be placed in the centrifuge. FIG. 5 will be described for the purpose of describing the protocol although it is understood that the wash cells could be those of FIGS. 3, 4 and the transfer/balance mechanism could be that of FIG. 10. The wash bag 1 is placed in one of the washing cells 100. Each bag is inserted into the socket 111 of a diaphragm 110 within the four wash cells. The two flaps 105, 106 of the lids of the washing cells 100 are closed and consequently secure the top of the wash bags 1 to the washing cells 100. The tube sensor 74 embedded in the outer flap 106 of the lid now faces the proximal end of the tube 4 connecting the wash bags 1 to the supernatant or satellite bag 2. The satellite bags 2 and optionally 3 are placed in the center 34. The satellite bags 2 and optionally 3 are each optionally placed in direct contact with pouches 81, 82, 83, and the fourth pouch of the optional second balancing mechanism. The tube 4 is inserted in the groove 72 of the first pinch valve membrane 70. If the bag set of FIG. 2 is used the tube 6 is inserted in the groove 72 of the second pinch valve member 71. The pinch valve members 70 and 71 are closed and the breakable stopper 11 is opened.

The rotor is then balanced in order to compensate for the difference in weights of the separation bags resulting in weight variation between the washing cells.

At the onset of this balancing stage, the pinch valve members 70 and 72, in which the tubes 4 and optionally 6 are engaged, are closed. The valve 123 on the conduit connecting the reservoir 120 to the rotor duct 56 is opened. The rotor is set in motion by the centrifuge motor 36 and its rotation speed increases steadily until it rotates at a predetermined speed to separate the red blood cells from the supernatant. During rotation, the rotor reaches a threshold speed at which its rotation causes the pumping of hydraulic liquid from the reservoir 120 into the interconnected hydraulic chambers 103 of the washing cells 100. The valve 123 is closed after a predetermined time sufficient to allow hydraulic fluid for balancing the rotor to be transferred into the hydraulic chambers 103. Because the hydraulic chambers 103 are interconnected by the peripheral manifold 52, the hydraulic liquid gets automatically distributed in the washing cells 100 so as to balance the rotor. When the weights of the washing bags 1 are the same, the distribution of the hydraulic liquid is even. When they are not, the distribution of the hydraulic liquid is uneven, and the smaller the weight of blood in a specific washing bag 1, the larger the volume of the hydraulic fluid in the associated hydraulic chamber 103.

The washed blood cells are sedimented out or separated from the washing solution and any other residual cells or plasma when the rotor reaches a sedimentation speed (about 3200 RPM, usually referred to as "hard spin").

The rotor is rotated at the selected sedimentation speed for a predetermined period of time that is selected so that, whatever the hematocrit of the red blood cells in the wash bag 1, the red blood cells sediment from the supernatant. Since, as mentioned above, the density of the hydraulic liquid is selected so as to be between the density of the packed red cells and the density of the wash solution, the wash bag 1 will take a hour-glass shape at the end of the sedimentation stage, as shown in FIG. 8.

The supernatant is then transferred to bag 2. For this transfer, the four pinch valve members 70 controlling the access to the bag 2 are opened. Valve 123 is opened. This causes a decrease in pressure within the wash cells 100 and hydraulic liquid starts flowing again into the hydraulic chambers 103. The raising volume of hydraulic fluid in the hydraulic chamber 103 squeezes the wash bags 1 and causes the transfer of the supernatant which includes the wash solution and any residual cells or plasma into the first satellite bags 2 or 23. Because the hydraulic liquid has a lower density than the density of the packed red blood cells, the red blood cells remain at the bottom of the wash cell 100 and the wash bag 1 progressively collapse above the red cells as shown in FIG. 9. The rotor speed may be reduced during expression to reduce the pressure at which the supernatant is expressed.

When each tube sensor 74 detects blood cells, then the associated pinch valve member 70 is closed. When the volumes of red blood cells in the four separation bags 1 are different, and/or the hematocrit of the red blood cells in the four wash bags 1 or 21 are different (which will be generally the case), then the four pinch valve members 70 close one after the other.

When the last pinch valve member 70 closes, the rotation speed of the rotor is decreased until the rotor stops. The hydraulic liquid simultaneously drains from the hydraulic chambers 103 into the reservoir 120. The red blood cells remain in the wash bag 1.

When this stage is completed, the four bag sets are removed from the separation apparatus and each bag set is separately handled manually.

If the bag set of FIG. 2 is used and it is desirable to leuko-reduce the red blood cells, the breakable stopper 10 blocking the communication between the wash bag 1 and the tube 6 connected thereto is broken, as well as the breakable stopper 14 blocking the communication between the second satellite bag 3 and the tube 6. The storage solution contained in the second satellite bag 3 is allowed to flow by gravity through the filter 13 and into the wash bag 1, where it is mixed with the red blood cells to lower the viscosity thereof. The content of the washing bag 1 is then allowed to flow by gravity through the filter 13 and into the second satellite bag 3.

Residual white blood cells and platelets may be trapped by the filter 13 so that substantially only red blood cells are collected in bag 3.

Alternatively the red blood cells may be expressed during centrifugation through the filter 3. In this embodiment another sensor is provided for controlling the expression of the red blood cells. To transfer the storage solution into the wash bag the hydraulic fluid flow may be reversed so that storage solution can flow from the satellite bag 3 in the center compartment, through the filter 13, to the wash bag 1. Using a lower centrifuge speed then that required for separation or sedimentation the storage solution is mixed with the red blood cells to reduce the viscosity thereof. The hydraulic fluid flow is then increased so that expression pressure is applied to the wash bag to express or push the red blood cells and the storage solution through the filter 13 to the satellite bag 3.

The above has been described without the optional second balancing mechanism. During the expression or squeezing stage, when the supernatant is transferred, the balancing liquid in the pouches 81, 82, 83 and the fourth pouch will self adjust due to the connecting tubing to compensate for the differences in weight in the satellite bags.

The above washing process can also be effective in reducing protein levels in red blood cells and thus possibly aid with respect to any subsequent viral inactivation or viral reduction procedures such as those described in U.S. Pat. No. 6,258,577.

Also the above washing process can be effective as a viral reduction or inactivation process even without further treatment.

As the washing process is effective at removing proteins it also can be used for removing prion proteins.

Figure 11:
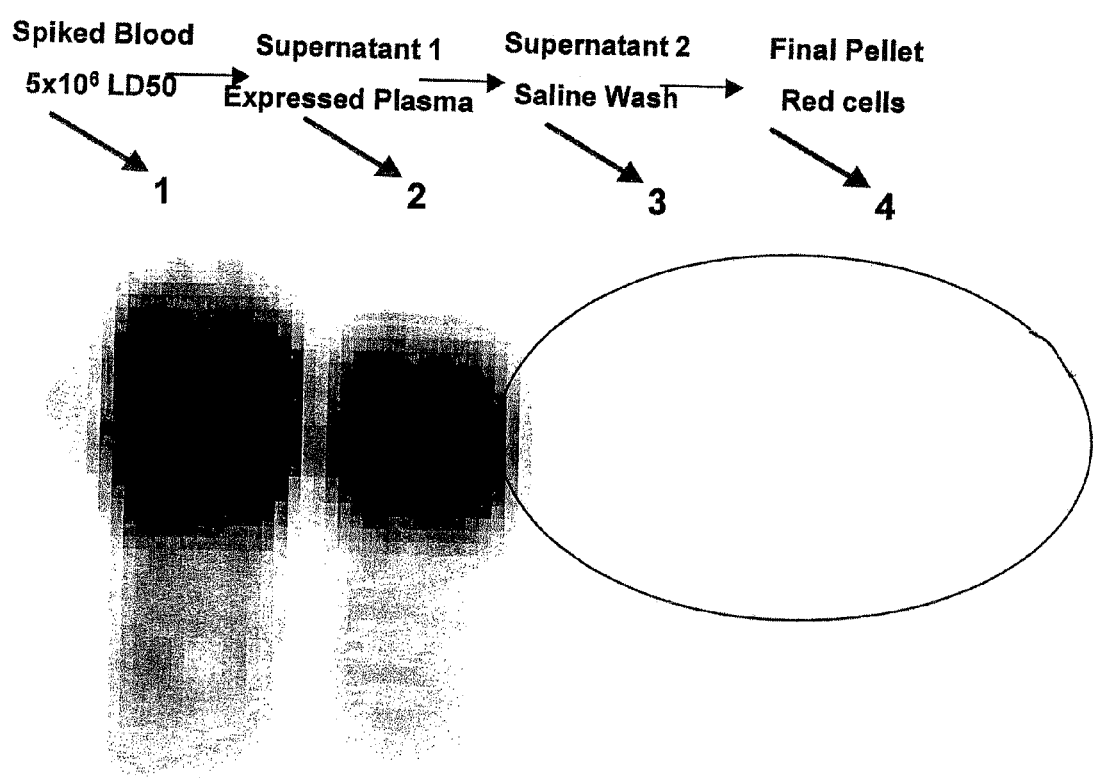
FIG. 11 is a Western Blot analysis showing prion reduction.

FIG. 11 shows the Western Blot Analysis for spiked whole blood as the initial product inoculated with hamster adapted scrapie 263K strain prion proteins. The initial product was inoculated at $5 \times 10^6$ LD50. Using the separation process of WO2007/001754 the plasma and other cells were expressed from the red blood cells. Following the wash process outlined above the resulting red blood cell product was washed in 300 mL of saline. FIG. 11 also shows the Western Blot Analysis for the expressed plasma and for the supernatant and residual red blood cells. No detectable prions were observed in the saline wash or the final red blood cell product as shown by the area in the oval.

Figure 12:
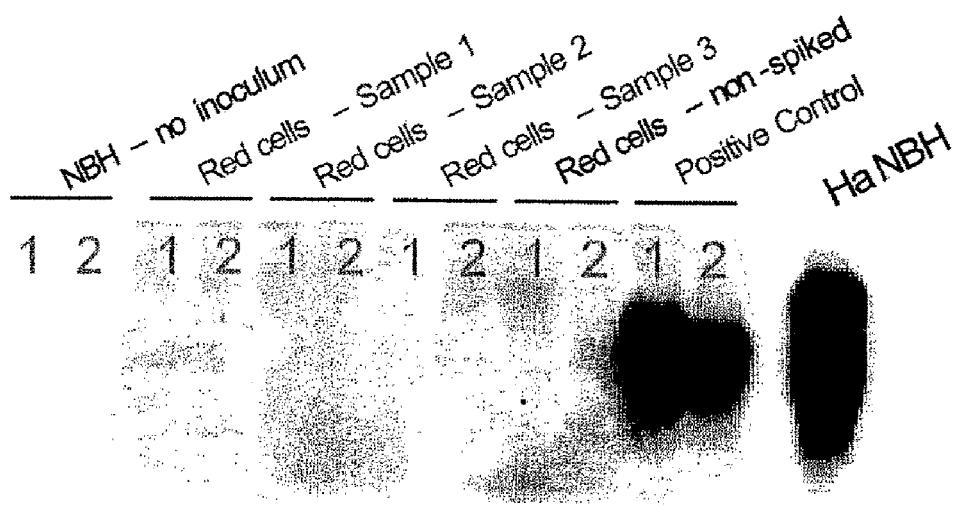
FIG. 12 is a PMCA analysis showing prion reduction.
Figure 12:
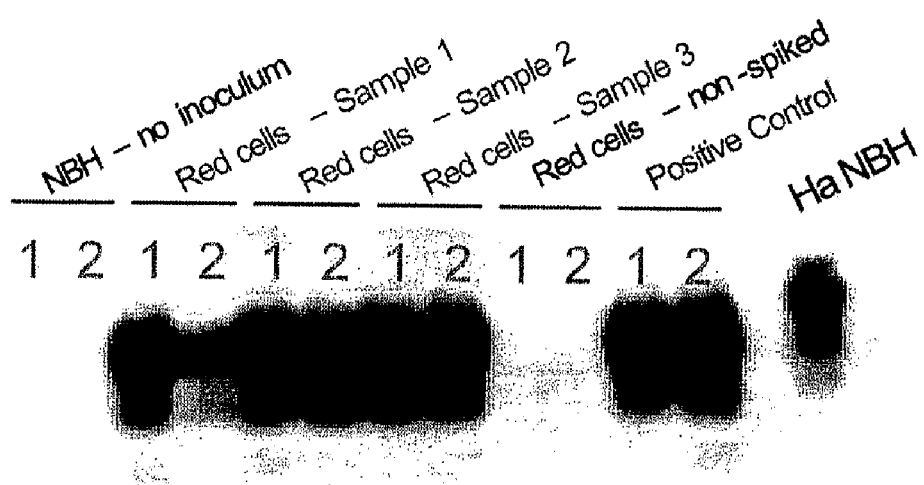

The analysis was continued using PMCA protein misfolding cyclic amplification studies. The PMCA study is shown in FIG. 12. The positive control sample was spiked whole blood without washing. The negative control sample is NBH or natural brain homogenate with no inoculum and non-spiked red blood cells. The spiked washed red blood cells are indicated as samples 1, 2, or 3.

Round 1 amplification also shows no prion proteins in the spiked samples. Only during second round amplification can any residuals be detected. It is estimated that 99.9% or 3 logs of protein including prion protein removal occurs during a 300 mL saline wash using the apparatus described above. The log removal amount is based on the protein amount of whole blood prior to separation and removal. It is calculated that an additional second wash step of adding through the same or additional tubing a second 300 mL of saline wash solution with subsequent expression of the second batch of supernatant as described above would remove 99.999% in the process. It is estimated to be 5 logs total of protein reduction including prior protein reduction as compared to the protein amount of whole blood.

Washing also removes extra cellular viral agents or pathogens. Whole blood was spiked with virus and then separated with the separated red blood cells being washed as described above. The virus or pathogen reduction levels are shown in the table below for red blood cells spiked with tissue culture infectious dose 50. All the data shown is with 4 replicates except for that of CPV which has 3 replicates.

| Pathogen | Log Reduction | Type |
|---|---|---|
| BVDV | 3.0-4.7 | Enveloped |
| HIV | >3.9->4.2 | Enveloped |
| HAV | 3.4-4.5 | Non-Enveloped |
| CPV | 3.4-4.1 | Non-Enveloped |

Figure 13:
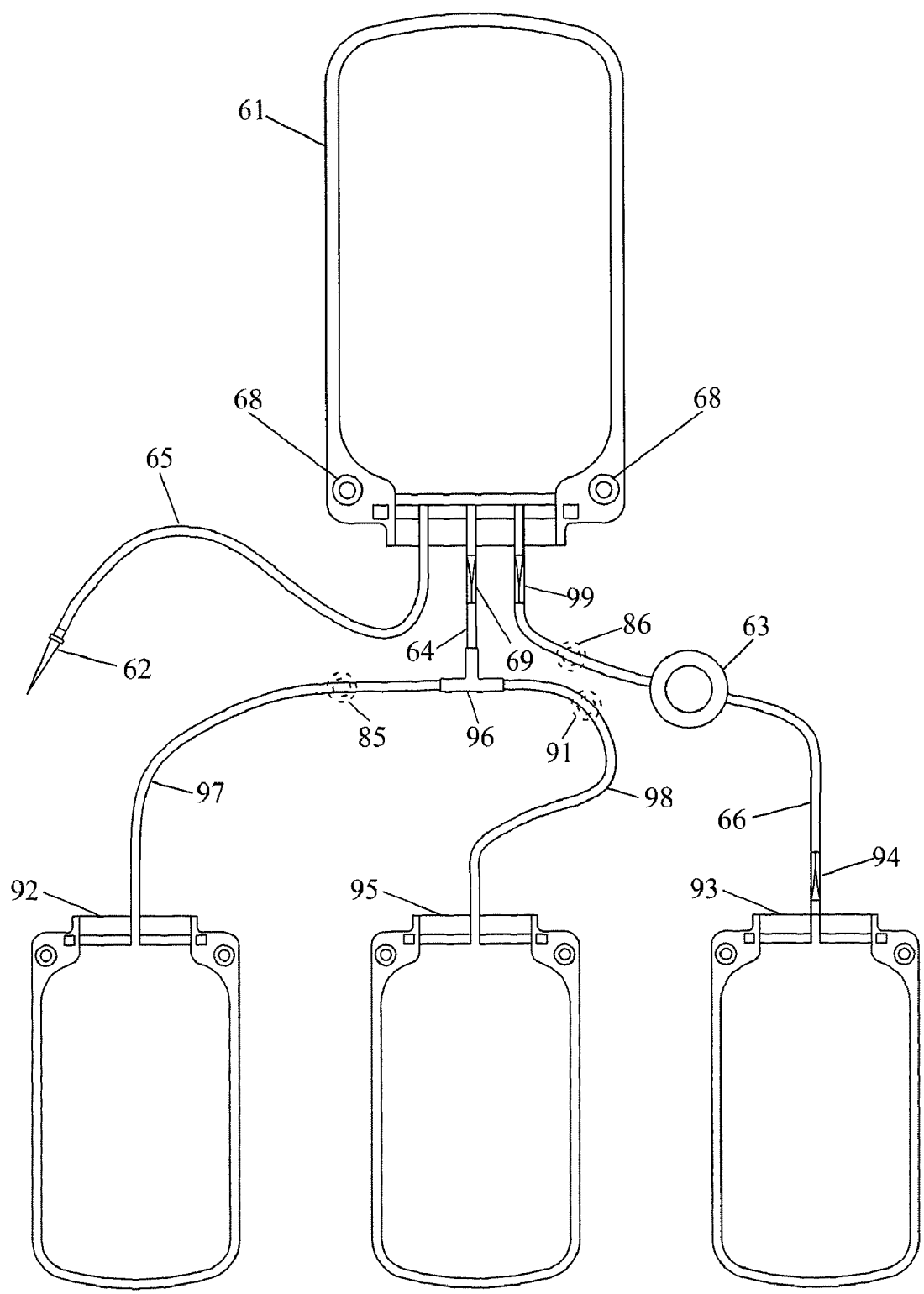
FIG. 13 is a schematic view of a bag set for separating a composite fluid such as whole blood and for washing one of the separated components for use with a centrifuge in accordance with the instant invention.

Although the above has been described with respect to red blood cells after separation it is understood that similar apparatus could be used to separate whole blood into components with subsequent washing of the desired component. For a whole blood process using the bag set of FIG. 13, the whole blood would be loaded into wash/separation bag 61. The associated centrifuge, such as those described above, would be rotated at a hard spin to separate the whole blood into components with the plasma being expressed, when valve and optional frangible or breakable connector 69 is open, and valve 85 is open, through conduit or tube 64, t-shaped connector 96, conduit or tube 97 to satellite bag 92. Another satellite bag 95 could be added if a platelet collection was desired with the platelets being expressed, when valve 91 is opened, through optional frangible 69, through conduit 64, t-shaped connector 96, conduit 98 into satellite bag 95. Similarly, if a mononuclear cell collection was desired a fourth bag would also be provided. The wash solution could optionally be introduced into bag 61 through spike 62 and conduit or tube 65 and mixed manually with the red blood cells remaining in the wash/separation bag 61. This would be done while the centrifuge rotation was stopped. After rotation begins, as described in the wash process above, the supernatant would be expressed into one of the satellite bags or an additional bag if needed. The washed red blood cells would then be either expressed or gravity drained into the satellite bag 93 through optional frangible 99, conduit 66, the filter 63 and frangible or breakable connector 94 if the bag set of FIG. 13 was used. Alternatively the wash/separation bag could be separated from the separation set of FIG. 13 and sterile docketed to one of the bag sets of FIGS. 1 and 2. The bag set of FIG. 13 with the associated separation protocol is described in International Application number PCT/US 2006/021827 or publication number WO 2007/001754. As described in this publication, separation bag 61 (also the wash bag) has a narrowed opening adjacent to the conduits or tubes 65, 64 and 66 to facilitate detection of some of the components by the sensors. The bag 61 also includes apertures or holes 68 for hanging. This procedure allows a single machine to be used for both separation and washing.

Figure 14:
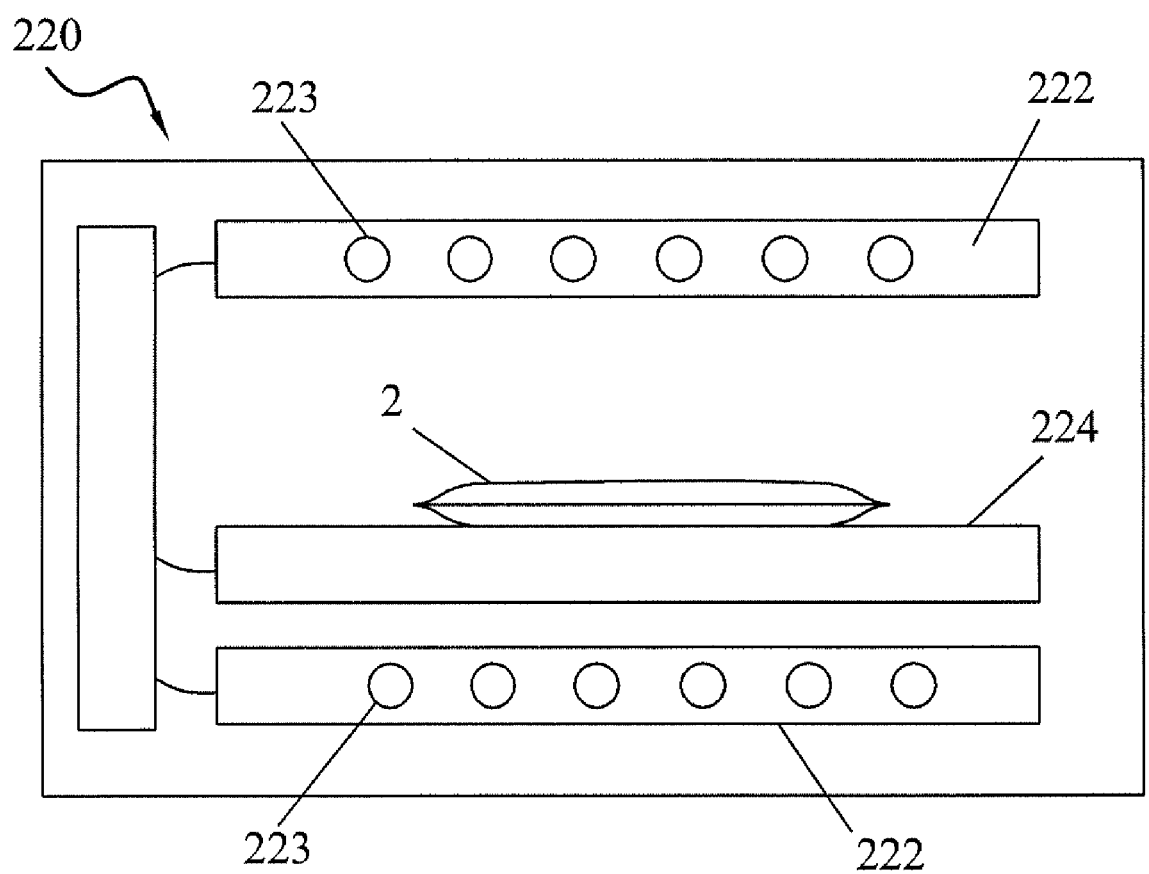
FIG. 14 is a schematic view of an illumination arrangement for illuminating a satellite bag in accordance with the instant invention.

As described above washing red blood cells after separation can reduce the viral or pathogen levels of these blood products. To further reduce the viral level, the washed cells may be subject to a subsequent viral inactivation process. As shown in FIG. 14, and using the bag set of FIG. 2 as an example, an endogenous alloxazine such as riboflavin or other photosensitizer may be added to the satellite bag 2 containing the washed product and light of suitable wavelength may be applied to activate the photosensitizer. FIG. 2 shows an illuminator 220 with light support 222 having lights 223 to illuminate satellite bag 2 on the platen 224. For riboflavin the light selected for illuminating the washed red blood cells would be UV light. It is anticipated this will reduce the pathogen content of this blood product to log reduction levels higher than those shown in the table above.

The systems and method described above permit the simultaneous washing of up to or greater than six red blood cell or other blood product or component units. It is believed each washing step will take a laboratory technician less than five minutes with the result being up to or greater than six washed units ready for use, storage or subsequent viral inactivation.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. A method of washing multiple units of blood product to remove any prions contained therein comprising
adding washing solution to each unit of blood product;
providing a centrifuge having a plurality of washing cells;
placing each unit of blood product with wash solution into a washing cell of the centrifuge;
rotating the centrifuge to sediment the blood product from supernatant including the washing solution in each unit of blood product;
balancing the centrifuge to accommodate for any variations in the washing cells; and
transferring the supernatant including any prions contained therein from each washing cell to leave washed blood product in each washing cell.

2. The method of claim 1 further comprising mixing the washing solution with the blood product.

3. The method of claim 1 wherein the blood product is red blood cells.

4. The method of claim 1 wherein the adding step comprises
adding washing solution to a wash bag containing each unit of blood product and the placing step comprises;
placing each wash bag containing wash solution and blood product in one of the plurality of washing cells.

5. The method of claim 4 wherein the transferring step comprises transferring the supernatant from each wash bag to a satellite bag.

6. The method of claim 5 further comprising placing each satellite bag in a center compartment around the rotational axis of the centrifuge.

7. The method of claim 1 wherein the balancing step comprises adding a fluid to each washing cell to correct for differences in the unit of blood product in the washing cell.

8. The method of claim 7 wherein the transferring step comprises adding sufficient fluid to each washing cell to squeeze the supernatant out of the washing cell.

9. The method of claim 8 wherein the adding step comprises
adding washing solution to a wash bag containing the unit of blood product; and
the transferring step comprises transferring the supernatant to a satellite bag fluidly connected to the wash bag.

10. A method of reducing proteins in a blood product comprising
collecting a plurality of units of blood product;
mixing each unit of blood product with washing solution;
adding each unit of blood product with washing solution to a wash cell on a centrifuge;
simultaneously centrifuging the plurality of units of blood product with washing solution to separate supernatant from the blood product;
removing the resulting supernatant including any proteins and washing solution from the centrifuging units;
reducing proteins in the blood product through the removing step.

11. The method of claim 10 wherein the protein to be removed includes any prion proteins.

12. The method of claim 10 further comprising balancing the centrifuge to accommodate for any differences in the units of blood product.

13. The method of claim 10 wherein the centrifuging step comprises sedimenting the blood product from supernatant including protein and wash solution.

14. The method of claim 12 wherein the balancing step comprises adding balancing fluid to a wash cell on the centrifuge containing each unit of blood product to accommodate for differences in the unit.

15. The method of claim 14 wherein the balancing fluid is hydraulic fluid.

16. The method of claim 14 wherein the removing step comprises adding additional balancing fluid to each wash cell to squeeze the supernatant out of the wash cell.

17. The method of claim 10 where in the blood product is red blood cells.

18. The method of claim 10 wherein the collecting step comprises collecting whole blood and separating the whole blood into at least the blood product.

19. The method of claim 10 wherein the method further comprises reducing the viral level of the blood product through the removing step.

20. The method of claim 19 further comprising
adding riboflavin to each unit of washed blood product; and
illuminating the riboflavin and washed blood product to further reduce the viral level.

* * * * *